(12) United States Patent
Choi

(10) Patent No.: US 10,006,164 B2
(45) Date of Patent: Jun. 26, 2018

(54) ELECTRIC IRON WITH ULTRAVIOLET STEAM DISINFECTION FUNCTION

(71) Applicant: Lung Wai Choi, Hong Kong (HK)

(72) Inventor: Lung Wai Choi, Hong Kong (HK)

( * ) Notice: Subject to any disclaimer, the term of this patent is extended or adjusted under 35 U.S.C. 154(b) by 11 days.

(21) Appl. No.: 15/413,445

(22) Filed: Jan. 24, 2017

(65) Prior Publication Data

US 2017/0130391 A1    May 11, 2017

Related U.S. Application Data

(63) Continuation-in-part of application No. 14/882,473, filed on Oct. 14, 2015, now Pat. No. 9,611,584.

(30) Foreign Application Priority Data

Mar. 13, 2015    (HK) .................................. 15102594

(51) Int. Cl.
| | | |
|---|---|---|
| *D06F 75/24* | (2006.01) | |
| *D06F 75/14* | (2006.01) | |
| *D06F 75/20* | (2006.01) | |
| *A61L 2/07* | (2006.01) | |
| *A61L 2/10* | (2006.01) | |
| *D06F 79/00* | (2006.01) | |

(52) U.S. Cl.
CPC ............ *D06F 75/246* (2013.01); *A61L 2/07* (2013.01); *A61L 2/10* (2013.01); *D06F 75/14* (2013.01); *D06F 75/20* (2013.01); *D06F 75/24* (2013.01); *D06F 79/00* (2013.01); *A61L 2202/26* (2013.01)

(58) Field of Classification Search
CPC .......... D06F 75/14; D06F 75/20; D06F 75/24; D06F 75/246; D06F 79/00; A61L 2/07; A61L 2/10; A61L 2202/11; A61L 2202/26; A61L 2209/212

See application file for complete search history.

(56) References Cited

U.S. PATENT DOCUMENTS

| | | | | |
|---|---|---|---|---|
| 3,906,187 | A | * 9/1975 | Turoczi, Jr. ............. | D06F 75/08 219/245 |
| 4,414,037 | A | * 11/1983 | Friedheim ................. | B08B 3/02 122/40 |
| 4,623,467 | A | * 11/1986 | Hamlin ................... | B01D 61/08 210/257.2 |
| 4,835,363 | A | * 5/1989 | Hoffmann ............. | D06F 75/246 219/228 |
| 5,324,423 | A | * 6/1994 | Markham .............. | H05B 41/36 210/192 |
| 9,322,124 | B1 | * 4/2016 | Al-Hasan ................ | D06F 58/10 |

FOREIGN PATENT DOCUMENTS

| | | |
|---|---|---|
| CN | 202740549 U | 2/2013 |
| CN | 203807833 U | 9/2014 |
| JP | 2016101246 A * | 6/2016 |

* cited by examiner

*Primary Examiner* — Ismael Izaguirre

(57) ABSTRACT

An electric iron includes an iron body defining a steam generation chamber for generation of steam; an iron sole plate formed at a bottom portion of the iron body and provided with an electric heating pipe; a steam nozzle formed on the iron sole plate and being in communication with the steam generation chamber; and an ultraviolet generation device mounted inside the steam generation chamber. The electric heating pipe heats up water supplied to the iron body and produces steam which is disinfected by ultraviolet generated by the ultraviolet generation device.

12 Claims, 5 Drawing Sheets

ELECTRIC IRON WITH ULTRAVIOLET STEAM DISINFECTION FUNCTION

CROSS-REFERENCE TO RELATED APPLICATIONS

This application is a Continuation-In-Part Application of U.S. patent application Ser. No. 14/882,473 filed on Oct. 14, 2015, which claims the benefit of Hong Kong Short-term Patent Application No. 15102594.9 filed on Mar. 13, 2015, the entire content of which is hereby incorporated by reference.

FIELD OF THE TECHNOLOGY

The present application relates to an electric iron with ultraviolet steam disinfection function.

BACKGROUND

An electric iron has been a tool widely used for pressing clothing and fabric. It has become an indispensable electric appliance in nowadays family, laundry shop and hotel, etc. Existing electric iron possesses steaming function. Water is added in a water tank of an electric iron and steam can be produced when in use. However, water and steam may remain in the water tank and other interior parts of the electric iron. This may lead to bacterial growth inside the electric iron after using the electric iron for a long period of time. When ironing clothing, water with bacteria will be ejected and will remain on the clothing. This becomes a potential threat to a user's health.

Also, operation of traditional electric irons is rather complicated. Before ironing, a user needs to select a suitable temperature level according to the material of clothing to be ironed. Selection of unsuitable temperature will lead to bad ironing effect and even permanent damage to the clothing.

SUMMARY

An object of the present application is to provide an electric iron with ultraviolet steam disinfection function. It can carry out ultraviolet disinfection on steam such that the electric iron is more hygienic and safe.

The electric iron with ultraviolet steam disinfection function provided in the present application includes an iron body defining a steam generation chamber for generation of steam; an iron sole plate formed at a bottom portion of the iron body and provided with an electric heating pipe; a steam nozzle formed on the iron sole plate and being in communication with the steam generation chamber; and an ultraviolet generation device mounted inside the steam generation chamber; whereby the electric heating pipe heats up water supplied to the iron body and produces steam which is disinfected by ultraviolet generated by the ultraviolet generation device.

The iron body may further include a water tank, and the water tank is in communication with the steam generation chamber.

A water pump may be provided between the water tank and the steam generation chamber for pumping water from the water tank to the steam generation chamber.

The steam nozzle may be directly facing the ultraviolet generation device such that part of the ultraviolet generated by the ultraviolet generation device emits from the steam nozzle.

The iron body may be provided with a control circuit board and a safety switch, the ultraviolet generation device and the safety switch being respectively connected with the control circuit board, and when power is supplied to the electric iron and the iron body is close to a fabric, the safety switch is activated and the control circuit board turns on the ultraviolet generation device, and when the iron body is far away from the fabric and the safety switch is de-activated, the control circuit board turns off the ultraviolet generation device.

The safety switch may be a photoelectric sensor or a mechanical micro switch.

The ultraviolet generation device may be an ultraviolet tube.

The ultraviolet tube may use a wavelength of 240-260 nm.

The iron sole plate may be made of a metal alloy material.

The steam generation chamber may be located above the iron sole plate such that the iron sole plate becomes a bottom wall of the steam generation chamber.

The bottom wall of the steam generation chamber may be provided with a coating of diffuser agent.

The iron sole plate may have a fixed operation temperature.

BRIEF DESCRIPTION OF THE DRAWINGS

Specific embodiments of the electric iron will now be described by way of example with reference to the accompanying drawings wherein.

DETAILED DESCRIPTION

Figure 1:
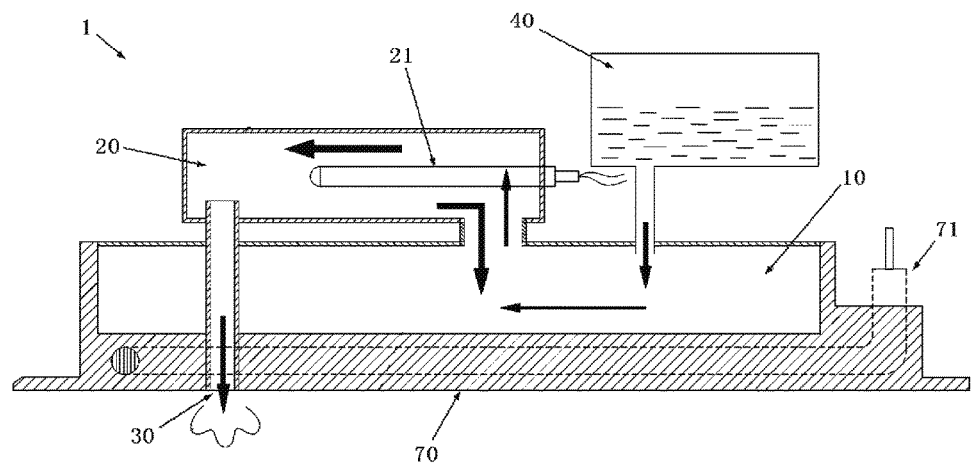
FIG. 1 is an illustrative diagram of the first embodiment of the electric iron with ultraviolet steam disinfection function of the present application.

To have a clear understanding of the technical features, objects and effects of the electric iron of present application, specific embodiments will now be described in detail with reference to the accompanying drawings.

Embodiments of the electric iron of the present application are described below in detail. These embodiments are shown in the accompanying drawings. Like reference numerals representing like parts are used throughout the drawings.

It should be appreciated that in the description of the present application, the term "front", "rear", "top", "bottom", etc. refers to the orientation or position of a structure as it is oriented and positioned in the drawings. Those terms are used to simplify the description and do not indicate or imply that the structure must have a specific orientation or operate in a specific position. Those terms should not be considered as limiting.

The electric iron with ultraviolet steam disinfection function of the present application includes an iron body. The iron body may have a steam generation chamber for steam generation. The iron body may further include an ultraviolet disinfection chamber for disinfecting steam generated in the steam generation chamber. The ultraviolet disinfection chamber can be in communication with the steam generation chamber. The ultraviolet disinfection chamber can be in communication with a steam nozzle of the iron body. An ultraviolet generation device may be provided inside the ultraviolet generation chamber for the generation of ultraviolet. During operation of the electric iron, water enters the steam generation chamber from a water tank and turns into steam by heat. The steam then enters the ultraviolet disinfection chamber. An ultraviolet generation device produces ultraviolet and carries out ultraviolet irradiation on the steam to kill bacteria, etc. in the steam. Steam particles become smaller after ultraviolet irradiation and can fully penetrate into fiber of the fabric to achieve a better ironing effect.

Various embodiments of the electric iron with ultraviolet steam disinfection function of the present application are described below.

FIG. 1 is an illustrative diagram of the first embodiment of the electric iron with ultraviolet steam disinfection function of the present application. In the embodiment, the electric iron includes an iron body 1. The iron body 1 may include a steam generation chamber 10 for the generation of steam. The steam generation chamber 10 may be in communication with a water tank 40. The water tank 40 may be an external water tank or an internal water tank for supplying water to the steam generation chamber 10. The electric iron may further include an ultraviolet disinfection chamber 20 for disinfecting steam generated in the steam generation chamber 10. An ultraviolet generation device 21 may be provided inside the ultraviolet generation chamber 20 for the generation of ultraviolet. The ultraviolet generation device 21 may be an ultraviolet tube. For example, it can be a quartz lamp tube that can emit ultraviolet, and preferably it can be an ultraviolet tube using a wavelength of 240-260 nm. The ultraviolet disinfection chamber 20 may be in communication with the steam generation chamber 10. Specifically, in the present embodiment, the ultraviolet disinfection chamber 20 can be located above the steam generation chamber 10. The ultraviolet disinfection chamber 20 can be communicated with the steam generation chamber 10 through a passageway or pipeline. Steam generated in the steam generation chamber 10 can enter the ultraviolet disinfection chamber 20 through the passageway or pipeline. The iron body 1 may be provided with a plurality of steam nozzles 30 for ejecting disinfected steam from the ultraviolet disinfection chamber 20. The ultraviolet disinfection chamber 20 can be in communication with the steam nozzles 30. Specifically, the ultraviolet disinfection chamber 20 can be communicated with the steam nozzles 30 through a passageway or pipeline. In the present embodiment, the iron body 1 may include an iron sole plate 70 made of a metal alloy material. The iron sole plate 70 may be provided with an electric heating pipe 71. The steam nozzles 30 can be disposed on the iron sole plate 70. The steam generation chamber 10 can be located above the iron sole plate 70 so that the iron sole plate 70 can become a bottom wall of the steam generation chamber 10. To achieve better steam generation, the bottom wall of the steam generation chamber 10 may be provided with a coating of diffuser agent.

During operation of the electric iron of the present embodiment, water flows into the steam generation chamber 10 from the water tank 40. When water falls on the iron sole plate 70 coated with a diffuser agent, i.e. on the bottom wall of the steam generation chamber 10, water turns into steam. Steam enters the ultraviolet disinfection chamber 20 through the passageway. The ultraviolet generation device 21 produces ultraviolet and carries out ultraviolet irradiation on the steam for sterilization and disinfection. Also, water condenses in the ultraviolet disinfection chamber 20 may flow back into the steam generation chamber 10 through the passageway where steam enters the ultraviolet disinfection chamber 20, and becomes steam again. Steam changes its small particle structure after ultraviolet disinfection and turns into a white mist form, which is heated again by the iron sole plate 70 when passing through the steam nozzles 30. The temperature of the steam in a mist form can reach above 100° C. Since the structure of small steam particles has changed, the small steam particles become smaller and can fully penetrate fiber of the fabric, thereby making the fabric moist and soft. It can produce a better ironing effect and achieve the function of sterilization and disinfection.

Figure 2:
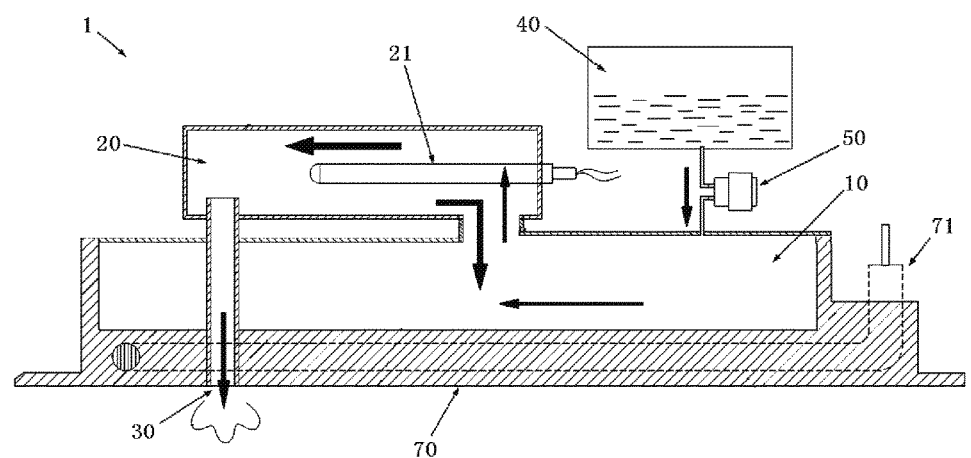
FIG. 2 is an illustrative diagram of the second embodiment of the electric iron with ultraviolet steam disinfection function of the present application.

FIG. 2 is an illustrative diagram of the second embodiment of the electric iron with ultraviolet steam disinfection function of the present application. The electric iron with ultraviolet steam disinfection function of this embodiment is an improvement on the first embodiment of the electric iron with ultraviolet steam disinfection function. Specifically, a water pump 50 may be provided between the water tank 40 and the steam generation chamber 10. Water from the water tank 40 can be pumped into the steam generation chamber 10 by the water pump 50. This structure is more suitable for electric iron with an external water tank, and suitable for situation where water tank is located at a farther distance from the steam generation chamber 10 such as a hanging iron and an industrial ironing equipment. The other structures of the electric iron of this embodiment are the same as those of the first embodiment and will not be repeated.

Figure 3:
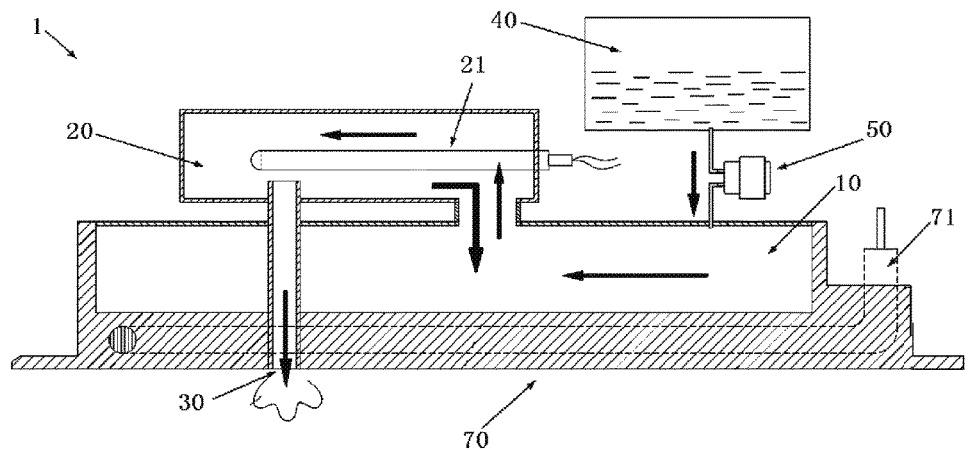
FIG. 3 is an illustrative diagram of the third embodiment of the electric iron with ultraviolet steam disinfection function of the present application.

FIG. 3 is an illustrative diagram of the third embodiment of the electric iron with ultraviolet steam disinfection function of the present application. The electric iron with ultraviolet steam disinfection function of this embodiment is an improvement on the second embodiment of the electric iron with ultraviolet steam disinfection function. Specifically, in order to produce a better sterilization and disinfection effect, the steam nozzles 30 can be directly facing the ultraviolet generation device 21 such that part of the ultraviolet generated by the ultraviolet generation device 21 can be emitted from the steam nozzles 30. This can be achieved by changing the relative position of the steam nozzles 30 and the ultraviolet generation device 21. During ironing, part of the ultraviolet generated by the ultraviolet generation device 21 can be emitted from the steam nozzles 30 and ultraviolet disinfection can be carried out on fiber of the fabric. The other structures of the electric iron of this embodiment are the same as those of the second embodiment and will not be repeated.

Figure 4:
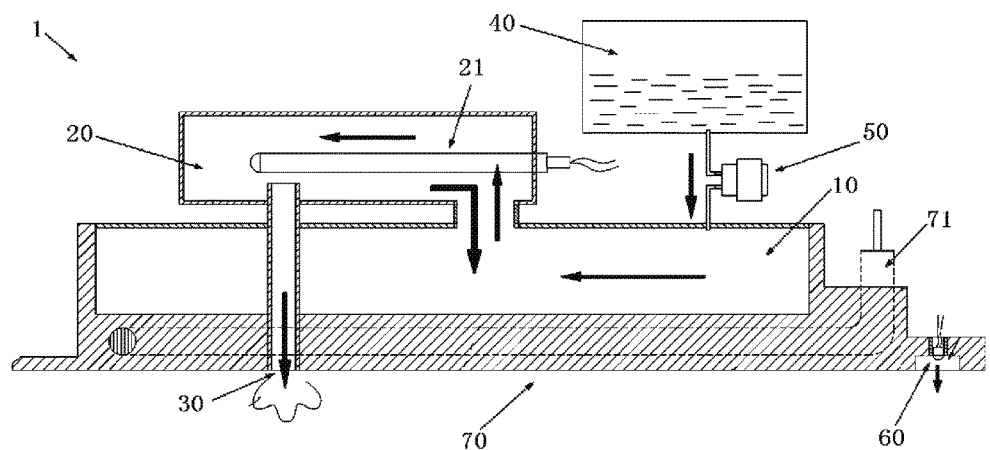
FIG. 4 is an illustrative diagram of the fourth embodiment of the electric iron with ultraviolet steam disinfection function of the present application.

FIG. 4 is an illustrative diagram of the fourth embodiment of the electric iron with ultraviolet steam disinfection function of the present application. The electric iron with ultraviolet steam disinfection function of this embodiment is an improvement on the third embodiment of the electric iron with ultraviolet steam disinfection function. Specifically, in order to prevent ultraviolet from emitting from the steam nozzles 30 and irradiating on a user or another person when the electric iron is not in use, the iron body 1 may be provided with a control circuit board (not shown) and a safety switch 60. The ultraviolet generation device 21 and the safety switch 60 can be respectively connected with the control circuit board. When power is supplied to the electric iron and the iron body 1 is close to the fabric, the safety switch 60 is activated and the control circuit board turns on the ultraviolet generation device 21. When the iron body 1 is far away from the fabric and the safety switch 60 is de-activated, the control circuit board turns off the ultraviolet generation device 21.

In the present embodiment, the safety switch 60 may be provided on the iron sole plate 70. The safety switch 60 can be a photoelectric sensor. During ironing, the photoelectric sensor does not detect light because the iron sole plate 70 is pressing on the fabric. The signal of the photoelectric sensor is ON and the control circuit board turns on the ultraviolet generation device 21 to emit ultraviolet. When the iron sole plate 70 is not pressing on the fabric or in any situation where light reception of the photoelectric sensor occurs, the signal of the photoelectric sensor is OFF and the control circuit board turns off the ultraviolet generation device 21. Hence, ultraviolet will not be irradiated on the user of the electric iron. This can achieve the function of safety and protection.

The safety switch 60 can also be a mechanical micro switch. During ironing, the mechanical micro switch is pressed because the iron sole plate 70 is pressing on the fabric. The signal of the mechanical micro switch is ON and the control circuit board turns on the ultraviolet generation device 21 to emit ultraviolet. When the iron sole plate 70 is not pressing on the fabric or when the mechanical micro switch is not pressed, the signal of the mechanical micro switch is OFF and the control circuit board turns off the ultraviolet generation device 21. Hence, ultraviolet will not be irradiated on the user of the electric iron.

The other structures of the electric iron of this embodiment are the same as those of the third embodiment and will not be repeated.

Figure 5:
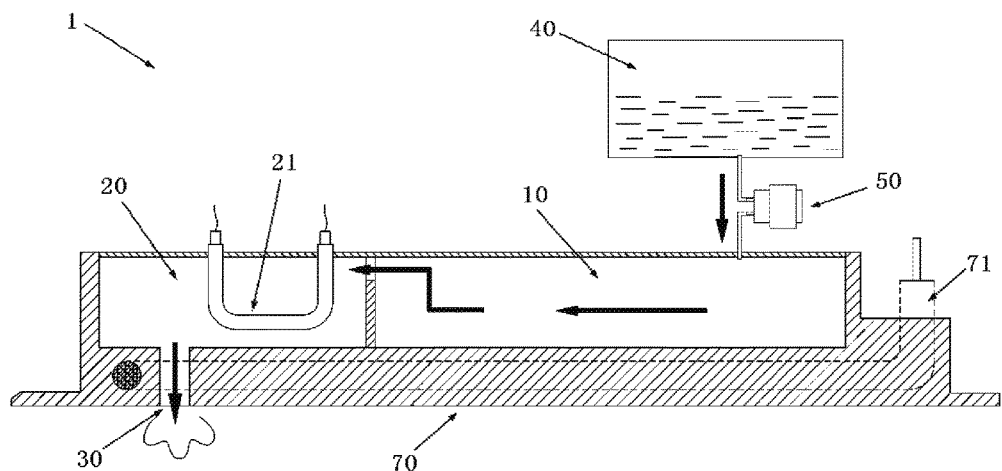
FIG. 5 is an illustrative diagram of the fifth embodiment of the electric iron with ultraviolet steam disinfection function of the present application.

FIG. 5 is an illustrative diagram of the fifth embodiment of the electric iron with ultraviolet steam disinfection function of the present application. The electric iron with ultraviolet steam disinfection function of this embodiment is an improvement on the second embodiment of the electric iron with ultraviolet steam disinfection function. Specifically, the ultraviolet disinfection chamber 20 is located in front of and adjacent to the steam generation chamber 10. The bottom wall of the ultraviolet disinfection chamber 20 can be formed by the iron sole plate 70. This can ensure that the ultraviolet disinfection chamber 20 has a relatively high temperature. This can prevent condensation and reduction of the amount of steam due to low temperature in the ultraviolet disinfection chamber 20. The other structures of the electric iron of this embodiment are the same as those of the second embodiment and will not be repeated.

Figure 6:
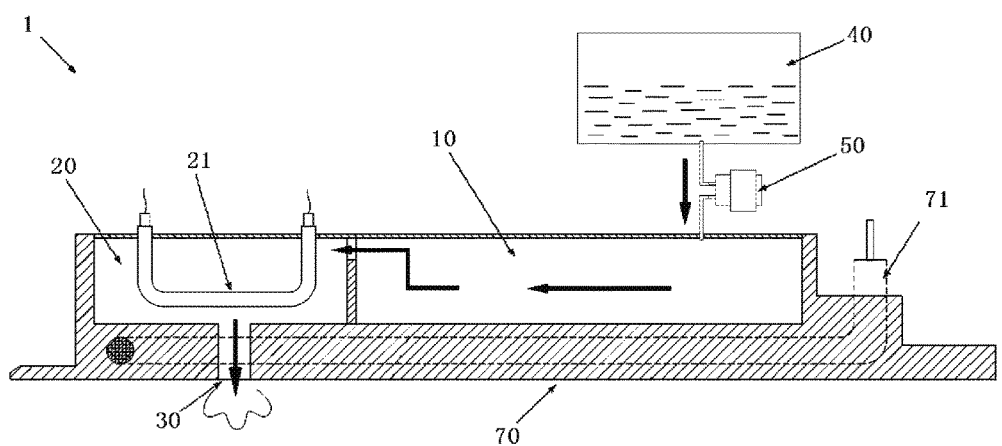
FIG. 6 is an illustrative diagram of the sixth embodiment of the electric iron with ultraviolet steam disinfection function of the present application.

FIG. 6 is an illustrative diagram of the sixth embodiment of the electric iron with ultraviolet steam disinfection function of the present application. The electric iron with ultraviolet steam disinfection function of this embodiment is an improvement on the fifth embodiment of the electric iron with ultraviolet steam disinfection function. Specifically, in order to produce a better sterilization and disinfection effect, the steam nozzles 30 can be directly facing the ultraviolet generation device 21 such that part of the ultraviolet generated by the ultraviolet generation device 21 can be emitted from the steam nozzles 30. This can be achieved by changing the relative position of the steam nozzles 30 and the ultraviolet generation device 21. During ironing, part of the ultraviolet generated by the ultraviolet generation device 21 can be emitted from the steam nozzles 30 and ultraviolet disinfection can be carried out on the fiber of the fabric. The other structures of the electric iron of this embodiment are the same as those of the fifth embodiment and will not be repeated.

Figure 7:
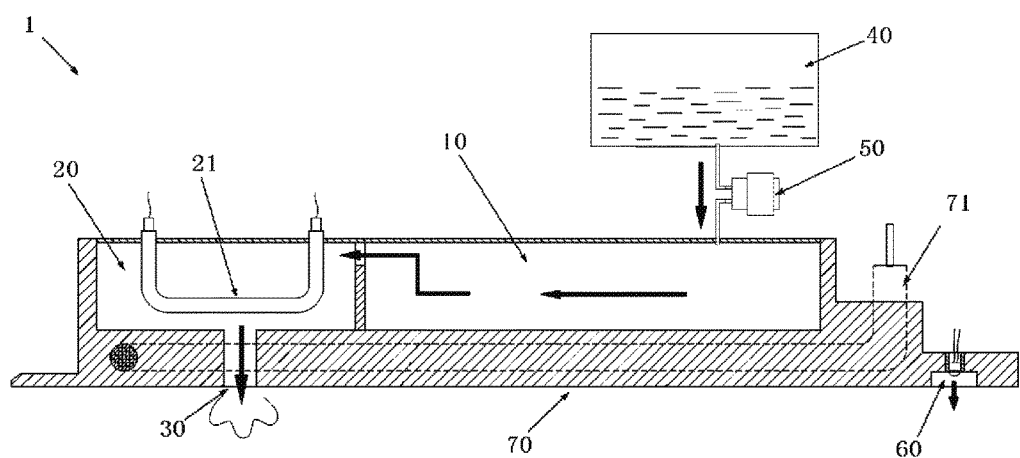
FIG. 7 is an illustrative diagram of the seventh embodiment of the electric iron with ultraviolet steam disinfection function of the present application.

FIG. 7 is an illustrative diagram of the seventh embodiment of the electric iron with ultraviolet steam disinfection function of the present application. The electric iron with ultraviolet steam disinfection function of this embodiment is an improvement on the sixth embodiment of the electric iron with ultraviolet steam disinfection function. Specifically, in order to prevent ultraviolet from emitting from the steam nozzles 30 and irradiating on a user or another person when the electric iron is not in use, the iron body 1 may be provided with a control circuit board (not shown) and a safety switch 60. The ultraviolet generation device 21 and the safety switch 60 can be respectively connected with the control circuit board. When power is supplied to the electric iron and the iron body 1 is close to the fabric, the safety switch 60 is activated and the control circuit board turns on the ultraviolet generation device 21. When the iron body 1 is far away from the fabric and the safety switch 60 is de-activated, the control circuit board turns off the ultraviolet generation device 21. The other structures of the electric iron of this embodiment are the same as those of the sixth embodiment and will not be repeated.

Figure 8:
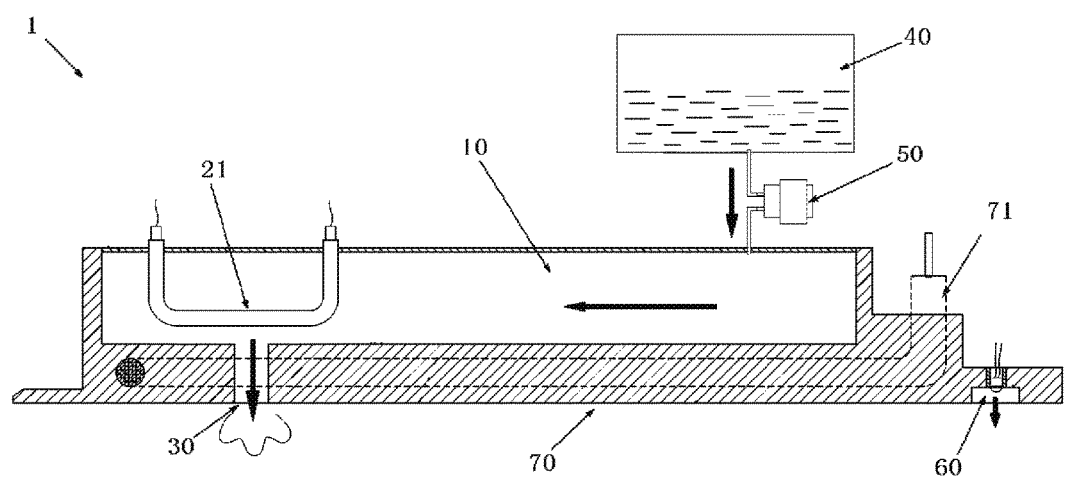
FIG. 8 is an illustrative diagram of the eighth embodiment of the electric iron with ultraviolet steam disinfection function of the present application.

FIG. 8 is an illustrative diagram of the eighth embodiment of the electric iron with ultraviolet steam disinfection function of the present application. In this embodiment, the iron body 1 may only include a steam generation chamber 10 for the generation of steam. The ultraviolet generation device 21 may be mounted inside the steam generation chamber 10.

The electric iron with ultraviolet steam disinfection function of the present application can produce ultraviolet disinfected steam. Since the steam particles produced are smaller, it can fully penetrate any fiber of a fabric, and can iron fabric of any clothing. Therefore, it is not necessary to provide a plurality of temperature levels, and can make operation easier for elderly people. Since it adopts a fixed temperature and the temperature is relatively low, it can save energy. For example, using the electric iron of the present application, a power of 980 W can reach the effect of current power of 2400 W. This can save 59% energy and will not scorch any clothing.

Specific embodiments have been described above with reference to the accompanying drawings. However, the present application is not limited to the above specific embodiments. The above specific embodiments are merely illustrative and should not be considered as limiting. It should be noted that, upon reading the above disclosure, a person skilled in the art can make various other changes or modifications without departing from the scope of the appended claims.

What is claimed is:

1. An electric iron, comprising an iron body defining a steam generation chamber for generation of steam; an iron sole plate formed at a bottom portion of the iron body and provided with an electric heating pipe; a steam nozzle formed on the iron sole plate and being in communication with the steam generation chamber; and an ultraviolet generation device mounted inside the steam generation chamber; whereby the electric heating pipe heats up water supplied to the iron body and produces steam which is disinfected by ultraviolet generated by the ultraviolet generation device.

2. The electric iron as claimed in claim 1, wherein the iron body further comprises a water tank, and the water tank is in communication with the steam generation chamber.

3. The electric iron as claimed in claim 2, wherein a water pump is provided between the water tank and the steam generation chamber for pumping water from the water tank to the steam generation chamber.

4. The electric iron as claimed in claim 1, wherein the steam nozzle is directly facing the ultraviolet generation device such that part of the ultraviolet generated by the ultraviolet generation device emits from the steam nozzle.

5. The electric iron as claimed in claim 4, wherein the iron body is provided with a control circuit board and a safety switch, the ultraviolet generation device and the safety switch being respectively connected with the control circuit board, and when power is supplied to the electric iron and the iron body is close to a fabric, the safety switch is activated and the control circuit board turns on the ultraviolet generation device, and when the iron body is far away from the fabric and the safety switch is de-activated, the control circuit board turns off the ultraviolet generation device.

6. The electric iron as claimed in claim 5, wherein the safety switch is a photoelectric sensor or a mechanical micro switch.

7. The electric iron as claimed in claim 1, wherein the ultraviolet generation device is an ultraviolet tube.

8. The electric iron as claimed in claim 7, wherein the ultraviolet tube uses a wavelength of 240-260 nm.

9. The electric iron as claimed in claim 1, wherein the iron sole plate is made of a metal alloy material.

10. The electric iron as claimed in claim 1, wherein the steam generation chamber is located above the iron sole plate such that the iron sole plate becomes a bottom wall of the steam generation chamber.

11. The electric iron as claimed in claim 9, wherein the bottom wall of the steam generation chamber is provided with a coating of diffuser agent.

12. The electric iron as claimed in claim 1, wherein the iron sole plate has a fixed operation temperature.

\* \* \* \* \*